United States Patent
Motoura et al.

[11] Patent Number: 5,943,549
[45] Date of Patent: Aug. 24, 1999

[54] METHOD OF EVALUATING SILICON WAFERS

[75] Inventors: Hisami Motoura; Kouichirou Hayashida, both of Kanagawa, Japan

[73] Assignee: Komatsu Electronics Metals Co., Ltd., Kanagawa, Japan

[21] Appl. No.: 08/998,757

[22] Filed: Dec. 29, 1997

[30] Foreign Application Priority Data

Dec. 27, 1996 [JP] Japan .................................... 8-357515

[51] Int. Cl.⁶ .............................. B44C 1/22; H01L 21/302
[52] U.S. Cl. .................................. 438/7; 216/85; 216/90; 216/99
[58] Field of Search ................................ 216/84, 85, 88, 216/89, 90, 99; 438/7

[56] References Cited

U.S. PATENT DOCUMENTS

| | | | |
|---|---|---|---|
| 3,765,956 | 10/1973 | Li | 148/33 |
| 5,271,796 | 12/1993 | Miyashita et al. | 156/626 |
| 5,374,582 | 12/1994 | Okonogi et al. | 437/63 |
| 5,843,322 | 12/1998 | Chandler, Jr. | 216/85 |

FOREIGN PATENT DOCUMENTS

| | | |
|---|---|---|
| 59-094828 | 5/1984 | Japan . |
| 60-148137 | 8/1985 | Japan . |
| 4-209532 | 7/1992 | Japan . |
| 5-226203 | 9/1993 | Japan . |
| 6-338548 | 12/1994 | Japan . |
| 7-206591 | 8/1995 | Japan . |
| 7-263429 | 10/1995 | Japan . |
| 8-70009 | 3/1996 | Japan . |

*Primary Examiner*—Benjamin Utech
*Assistant Examiner*—George Goudreau
*Attorney, Agent, or Firm*—Sughrue, Mion, Zinn, Macpeak & Seas, PLLC

[57] ABSTRACT

The method of evaluating silicon wafers according to this invention is capable of predicating degradation of the quality of oxide film insulation, which is incurred, on the silicon wafers, by process faults or local residual strains undetectable by the naked eye. The method includes the following steps of: removing selectively a surface of a silicon wafer treated by mirror polishing by using an etching selectivity caused by an unordinary surface state; counting the number of etch pits on the surface of the silicon wafer with the aid of an optical microscope; and judging the quality of the silicon wafer based on the etch pit density, which is calculated from the above number of etch pits, and the threshold value of etch pit density. The threshold value of etch pit density of the silicon wafer treated by selective etching is set to be below $5 \times 10^5$ pits/cm², and improvements to the processing of production lines relating to low-quality silicon wafers can be made.

5 Claims, 3 Drawing Sheets

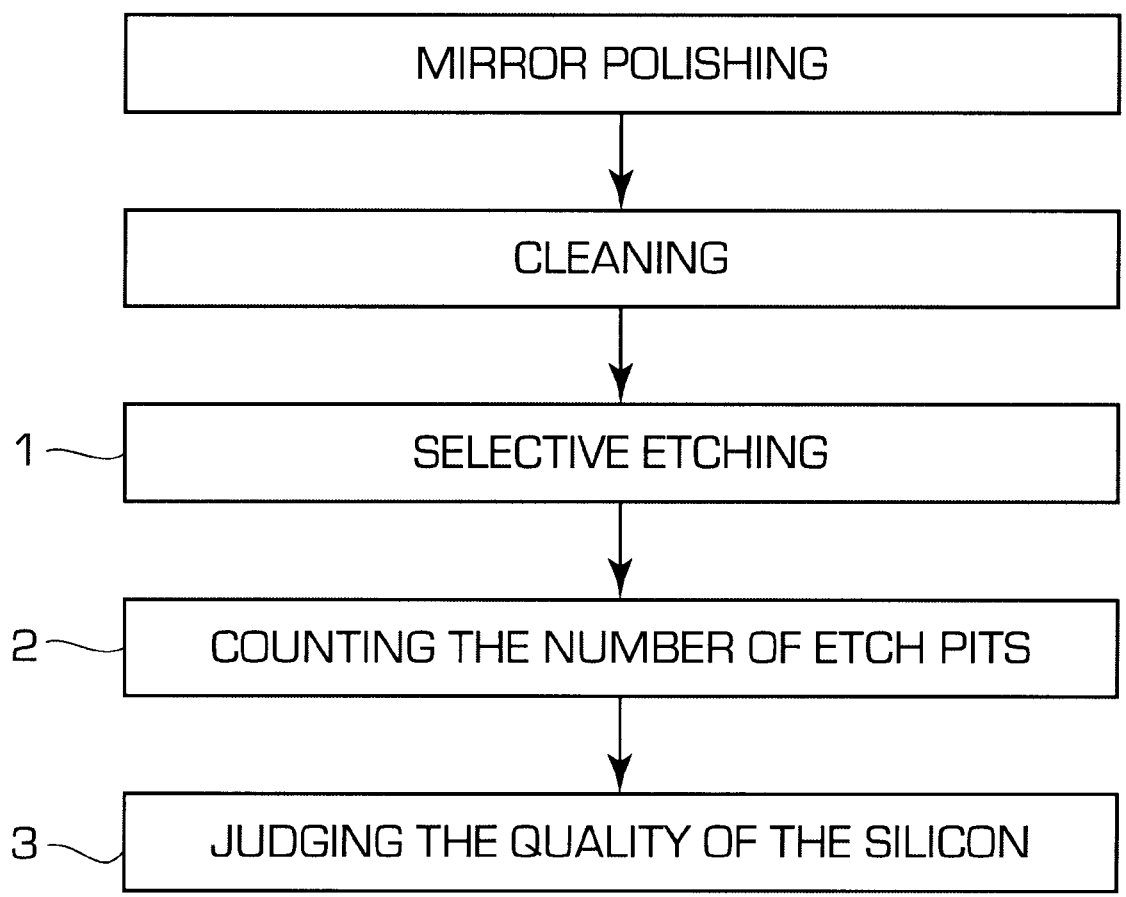

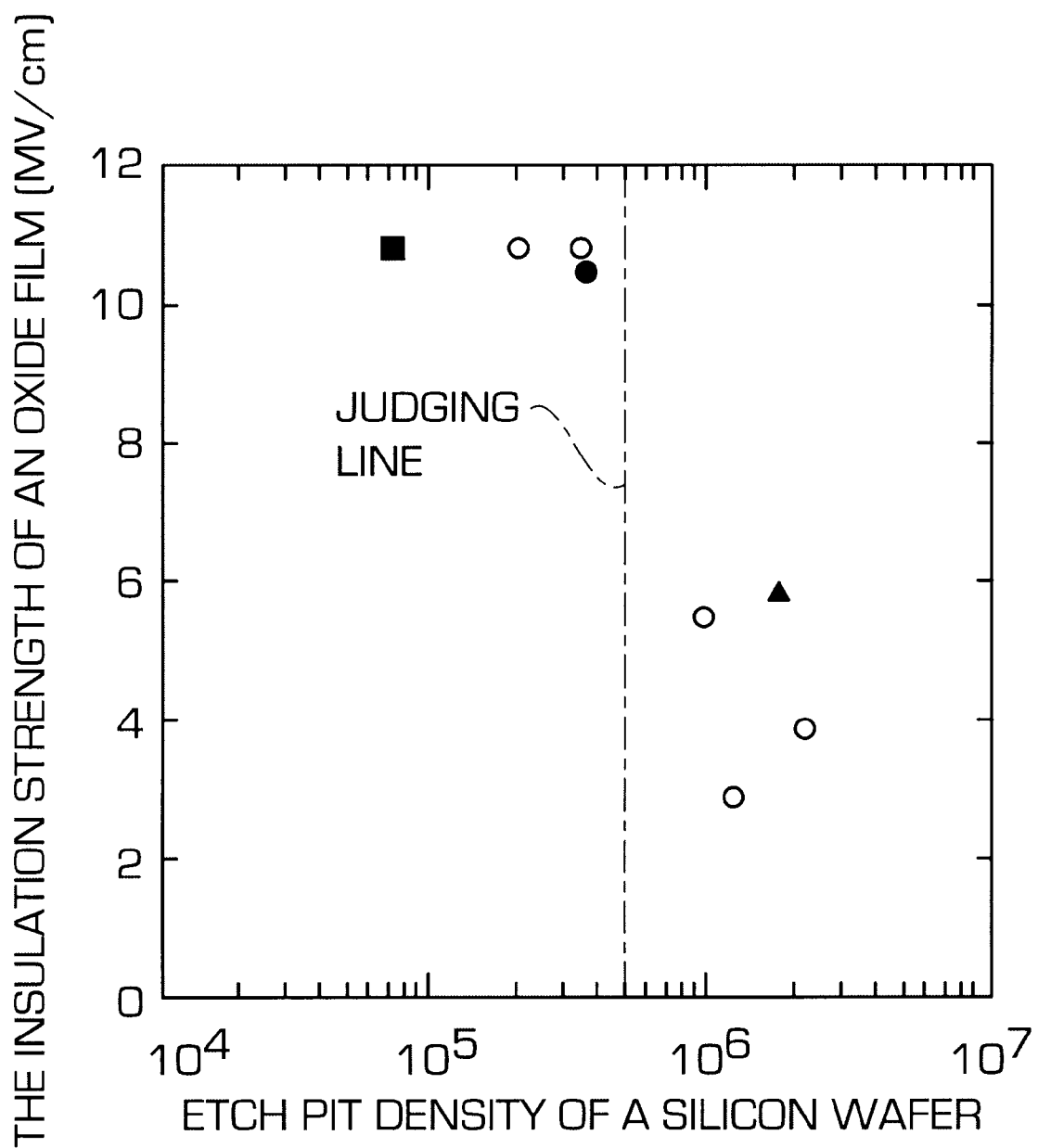

| ETCH | COMPOSITION [VOLUME] | RATE [mm/min] | PURPOSE | COMMENTS |
|---|---|---|---|---|
| SIRTL | HF(49%), $CrO_3$ (5M) = 1:1 | ~1 | OSF DISLOCATION | GOOD ON {111} |
| DASH | HF(49%), $HNO_3$(70%), $CH_3COOH$ = 1:3:12 | ~0.03 | OSF | GOOD ON ALL PLANES |
| SECCO | HF (49%), $K_2Cr_2O_7$ (0.15M) = 2:1 | ~1.5 | OSF DISLOCATION | GOOD ON {100} BEST IN ULTRASOUNDS |
| WRIGHT | HF(49%), $HNO_3$(69%), $CrO_3$(5M), $Cu(NO_3)_2$, $H_2O$, $CH_3COOH$ = 60ml:30ml:30ml:2g:60ml:60ml | ~1 | OSF BMD DISLOCATION | GOOD ON ALL PLANES BEST IN ULTRASOUNDS |
| SATO | HF(49%), $HNO_3$(69%), $CH_3COOH$ $H_2O$ = 1:15:3:1 | ~1.8 | OSF BMD | NON $Cr^{6+}$ (CHROMIUM) |
| SCHIMMEL | HF(49%), $CrO_3$(1M) = 2:1 | ~1.75 | DISLOCATION | LIGHTLY DOPED Si (0.6~15Ωcm) GOOD ON{100} NO ULTRASOUNDS |
| SCHIMMEL (MODIFIED) | HF(49%), $CrO_3$(1M), $H_2O$ = 2:1:15 | ~1.8 | DISLOCATION | HEAVILY DOPED Si GOOD ON{100} NO ULTRASOUNDS |

FIG. 3

METHOD OF EVALUATING SILICON WAFERS

BACKGROUND OF THE INVENTION

1. Field of the Invention

This invention relates to a method of evaluating silicon wafers, particularly to a method adapted to evaluate the quality of mirror polishing of silicon wafers and the quality of the grinding process for silicon wafers, which is an important factor affecting the quality of silicon wafers.

2. Description of Prior Art

Silicon wafers employed in semiconductor devices are sliced from silicon single crystals, which are usually manufactured by the CZ or FZ method. The outer peripheries of the sliced silicon wafers are chamfered, then processes such as grinding, lapping, and polishing are performed on both of the front and rear surfaces so as to mirror-finish at least one surface.

Grinding and polishing semiconductor wafers to be mirror-finished produces process faults (hereinafter referred as defects) such as scratching capable of being detected by eyesight inspection and local residual strains undetectable by the naked eye. According to JP-A 8-70009 (JP-A: Japanese unexamined Patent Publication) entitled "METHOD OF MANUFACTURING SEMICONDUCTOR SILICON WAFERS", the existence of residual strains undetectable by the naked eye can be recognized by using a microscope if selective etching is performed on a silicon wafer. Furthermore, the above residual strains can be removed by applying heat treatment to silicon wafers within a short time period at low temperature.

The above method of manufacturing semiconductor silicon wafers is adaptable for removing residual strains induced during mirror polishing on surfaces of silicon wafers, the result can be recognized by performing selective etching. However, even if selective etching has been performed, it is impossible to predict the extent to which the recognized defects will adversely affect the important qualities of semiconductor devices, for example the electrical characteristic such as oxide film insulation. Therefore, it is difficult to isolate the quality-control problems in the processing of silicon wafers and improve them.

SUMMARY OF THE INVENTION

In view of the above drawbacks, the object of the present invention is to provide a method of evaluating silicon wafers, which can contribute to the management and improvement of the processing of silicon wafers. The method of evaluating silicon wafers is capable of easily evaluating the relationship between the quality of oxide film insulation and the proceeding steps such as mirror polishing and washing.

A first aspect of the method of evaluating silicon wafers is a method according to this invention, which comprises the following steps of:

removing selectively a surface of a silicon wafer treated by mirror polishing by using a etching selectivity caused by unordinary surface state;

counting the number of etch pits on the surface of the silicon wafer by the aid of an optical microscope; and judging the quality of the silicon wafer based on the etch pit density, which is calculated from the above number of etch pits, and the threshold value of etch pit density.

A third aspect of the method of evaluating silicon wafers is a method according to the first aspect, wherein the step of removing is conducted after mirror polishing and washing the surface of a silicon wafer.

A fourth aspect of the method of evaluating silicon wafers is a method according to the first aspect, wherein the step of judging the quality of the silicon wafer comprises a step of judging the quality to be good in the case that the threshold value of etch pit density of the silicon wafer treated by selective etching is less than $5 \times 10^5$ pits/cm$^2$.

BRIEF DESCRIPTION OF THE DRAWINGS

The present invention can be more fully understood by reading the subsequent detailed description and examples with references made to the accompanying drawings, wherein:

FIG. 1 is a block diagram showing the sequence of the steps of evaluating silicon wafers;

FIG. 2 is a graph showing the relationship between the etch pit density of a silicon wafer and the insulation strength of an oxide film; and FIG. 3 represent a list of etching solutions used in the selective etching process.

DETAILED DESCRIPTION OF THE PREFERRED EMBODIMENT

After removing a layer of depth 0.5–5 μm by performing selective etching on the surface of a silicon wafer, the defects on the surface of the silicon wafer are capable of being enlarged to a size visible by the aid of an optical microscope. "Selective etching" used in the present invention is based on the steps of oxidizing a silicon wafer and being solved by hydrogen oxide. In the selective etching process, an oxidation rate caused by the oxidation agent in the defective region which has a crystal defect or strain is distinct from that in the complete crystal region (non-defective region). Namely, oxide formed in the defective region is usually etched preferably to be a concave shaped pit. On the other hand the defective region where etching rate gets slower, is etched to be convex shaped mount.

In the case that the step of etching is accompanied with plurality of reactions, etching rate are determined by the ratio of the etching agent (HF etc.) reaching to the surface of the crystal rather than the surface state of the crystal. Therefore by stirring an etching solution, the etching rate can be increased and the etching reaction advances uniformly. Alternatively, by adding the buffer agent (for example $H_2O$, $CH_3COOH$), the etching rate can be restrained. As the oxidizing agent is increased, the etched surface is apt to be made dim.

Therefore, etch pit density can be easily calculated, if the number of the etch pits appearing on the surface of the silicon wafer treated by selective etching is counted by the aid of the optical microscope.

An etch pit density obtained by following the above sequence was compared with a threshold value of etch pit density to judge the quality of processing the silicon wafer. It was found that only silicon wafers with etch pit density below $5 \times 10^5$ pits/cm$^2$ have an oxide film insulation larger than 8 MV/cm. Therefore, it is possible to properly judge whether the oxide film insulation satisfies the requirement of semiconductor devices or not. Then, improvements can be made to the silicon wafers judged as bad ones.

The following is a description of an embodiment of the method of evaluating silicon wafers, according to this invention with references made to the drawings. FIG. 1 is a block diagram showing the sequence of the steps of evaluating silicon wafers, wherein the numerals shown on the left side of each step denote the step numbers.

After performing mirror polishing, the surface of the silicon wafer was washed. Then, in the first step, the silicon wafer to be evaluated was etched to a depth of 0.5–5 μm by employing a selective etching solution consisting of HF: $HNO_3$: $CH_3COOH$: $H_2O$=1: 15: 3: X (wherein the volume ratio X is usually set to be 3). At the beginning of etching, the temperature of the selective etching solution was set to be 20–25° C. Then, in the second step, the surface of the silicon wafer etched by the above selective etching solution was inspected by the aid of an optical microscope, and the number of the etch pits existing on the surface of the silicon wafer was counted. In the third step, etch pit density was calculated, based on the number of the etch pits counted, and the etch pit density obtained was compared with a threshold value to judge the quality of the silicon wafer. On this occasion, the threshold value of etch pit density was set to be below $5 \times 10^5$ pits/$cm^2$. Next, silicon wafers judged as bad according to the above procedure were evaluated with respect to their fabrication conditions, and improvement was made, based on the above evaluation results.

To examine whether the threshold value of etch pit density of this invention is proper or not, the following experiment was carried out. A silicon wafer was heat-treated within an oxidation atmosphere so as to form a thermal oxide film on the wafer surface. The above silicon wafer was sliced under the same condition and was sliced from the same crystal as the silicon wafer whose etch pit density had been calculated by the aid of the optical microscope. Next, a polycrystalline silicon layer was formed on the above thermal oxide film by the CVD method. Then, a preset number of polycrystalline electrodes having a predetermined size were formed by photolithography technology. Through this procedure, MOS capacitors were constructed by disposing an insulation layer of thermal oxide film between the silicon wafer and the polycrystalline electrodes. Subsequently, an electrical voltage was applied between the silicon wafer and the polycrystalline electrodes so as to measure the insulation strength of the oxide film.

FIG. 2 shows the relationship between the etch pit density of the silicon wafer and the insulation strength of the oxide film in the above MOS capacitor structures. In FIG. 2, the symbols ■, ●, ▲, respectively denote silicon wafers mirror polished under polishing conditions A, B, and C. Furthermore, the symbol "O" denotes the wafers proceeded under B polishing condition and already being treated to change its surface state. Based on the results of measuring the insulation strength, the above wafers were classified into two groups. In other words, they were classified into a high-quality group having insulation strengths larger than 10 MV/cm and a poor-quality group having insulation strengths ranging from 2 to 6 MV/cm. The etch pit densities of the high-quality group were located to the left side of a quality judgment line, in other words, the values of their insulation strength were less than $5 \times 10^5$ pits/$cm^2$. The etch pit densities of the poor-quality group were located to the right side of the quality judgment line, namely, the values of their insulation strength were larger than $5 \times 10^5$ pits/$cm^2$. The above measurement confirmed that wafers having etch pit densities less than $5 \times 10^5$ pits/$cm^2$ have good insulation.

As above described, conventionally, the influence of mirror polishing of silicon wafers on the insulation was difficult to predict. However, according to this invention, the quality of the mirror polishing of silicon wafers can be easily evaluated by only measuring etch pit densities of the wafers subjected to mirror polishing and selective etching. Therefore, it is possible to evaluate the quality of proceedings without performing the evaluation of oxide film insulation, and it is possible to manage and improve the processing of silicon wafers.

As an etching solution used in a selective etching process, etching solutions as shown in FIG. 3 can be used. It is preferable to use a solution without containing Chromium in the view of a problem of treatment of waste liquid.

Furthermore, the evaluation method of this invention is not limited to the evaluation of the mirror polishing of silicon wafers. It also can be used as a simple substitute procedure for evaluating the electric characteristics of a silicon wafer.

What is claimed is:

1. A method of evaluating silicon wafers comprising the steps of:

mirror polishing and washing a surface of a silicon wafer, on which a gate oxide insulation film is to be formed;

removing selectively a portion of the surface of the silicon wafer through a selective etching process that highlights the defective regions of the surface;

counting the number of defects on the surface using an optical microscope; and evaluating the quality of the oxide insulation film to be formed based on the total number of defects on the surface and a threshold value of defects.

2. A method as claimed in claim 1, wherein the step of removing selectively a portion of the surface of the silicon wafer uses a selective etching solution comprising HF, $HNO_3$, $CH_3COOH$, and $H_2O$.

3. A method of evaluating silicon wafers as claimed in claim 1, wherein the step of removing comprising the steps of:

oxidizing said surface with an oxidation agent, wherein an oxidation rate of a defect region of said surface, caused by said agent, is distinct from an oxidation rate of a non-defect region of said surface, where said defect region is a region of said surface having crystal defects or strain; and selectively etching away a portion of said oxidized surface formed in said oxidizing step, with an etching agent.

4. A method of evaluating silicon wafers as claimed in claim 3, wherein said etching agent is HF.

5. A method of evaluating silicon wafers as claimed in claim 3, wherein said oxidizing step and said etching step are performed simultaneously in a solution comprising HF, $HNO_3$, $CH_3COOH$, and $H_2O$.

* * * * *